United States Patent [19]
Fishbine et al.

[11] Patent Number: 5,467,403
[45] Date of Patent: * Nov. 14, 1995

[54] PORTABLE FINGERPRINT SCANNING APPARATUS FOR IDENTIFICATION VERIFICATION

[75] Inventors: Glenn M. Fishbine, Eden Prairie; Robert J. Withoff, Minnetonka; Theodore D. Klein, Mound, all of Minn.

[73] Assignee: Digital Biometrics, Inc., Minnetonka, Minn.

[*] Notice: The portion of the term of this patent subsequent to Jun. 22, 2010, has been disclaimed.

[21] Appl. No.: 40,878

[22] Filed: Mar. 31, 1993

Related U.S. Application Data

[63] Continuation-in-part of Ser. No. 794,476, Nov. 19, 1991, Pat. No. 5,222,152.

[51] Int. Cl.⁶ ..................................................... G06K 9/22
[52] U.S. Cl. ......................... 382/116; 382/127; 382/313; 348/158; 340/825.34
[58] Field of Search ........................ 382/2, 4, 5, 59; 358/93, 108; 356/71; 340/825.3, 825.31, 825.34; 348/61, 77, 156, 158

[56] References Cited

U.S. PATENT DOCUMENTS

| | | | |
|---|---|---|---|
| Re. 33,572 | 4/1991 | Meyers | 250/504 R |
| 3,968,476 | 7/1976 | McMahon | 382/4 |
| 4,210,899 | 7/1980 | Swonger et al. | 382/5 |
| 4,338,025 | 7/1982 | Engel | 356/71 |
| 4,449,189 | 5/1984 | Feix et al. | 395/2.82 |
| 4,516,157 | 5/1985 | Campbell | 348/158 |
| 4,811,414 | 3/1989 | Fishbine et al. | 382/52 |
| 4,821,118 | 4/1989 | Lafreniere | 382/4 |
| 4,843,377 | 6/1989 | Fuller et al. | 340/573 |
| 4,896,363 | 1/1990 | Taylor | 382/5 |
| 4,933,976 | 6/1990 | Fishbine et al. | 382/4 |
| 5,054,090 | 10/1991 | Knight et al. | 382/4 |
| 5,059,778 | 10/1991 | Zouzoulas et al. | 235/472 |
| 5,077,612 | 12/1991 | Megrgardt et al. | 358/209 |
| 5,105,467 | 4/1992 | Kim et al. | 382/4 |
| 5,121,407 | 6/1992 | Partyka et al. | 375/1 |
| 5,202,929 | 4/1993 | Lemelson | 382/2 |
| 5,222,152 | 6/1993 | Fishbine | 382/2 |

FOREIGN PATENT DOCUMENTS

| | | |
|---|---|---|
| 0101772 | 3/1984 | European Pat. Off. . |
| 2501516 | 7/1976 | Germany . |
| WO91/07728 | 5/1991 | WIPO . |

Primary Examiner—Michael T. Razavi
Assistant Examiner—Larry J. Prikockis
Attorney, Agent, or Firm—Merchant, Gould, Smith, Edell, Welter & Schmidt

[57] ABSTRACT

A portable and lightweight fingerprint scanning apparatus which can optically scan and record fingerprint images in the field and transmit said images to a mobile unit for processing and subsequent wireless transmission to a central location for the purpose of providing immediate identity and background checks on the individual being fingerprinted. The apparatus of the present invention includes a fingerprint scanner for capturing a fingerprint image, a camera for capturing a photographic image of a person or a scene and means for transmitting the fingerprint image and the photographic image to a mobile unit. In the preferred embodiment the present invention includes a highly integrated camera with a superior signal to noise ratio and an infrared lighting source for illuminating a person or scene in low ambient light situations. An especially preferred embodiment of the present invention also provides the ability to preview the fingerprint and "mug shot" images on a display screen and to control transmission and processing of the fingerprint and "mug shot" images by the mobile unit using a terminal or keypad located on the portable fingerprint scanning apparatus.

4 Claims, 5 Drawing Sheets

PORTABLE FINGERPRINT SCANNING APPARATUS FOR IDENTIFICATION VERIFICATION

This is a continuation-in-part of prior application Ser. No. 07/794,476, filed on Nov. 19, 1991, now U.S. Pat. No. 5,222,152, issued on Jun. 22, 1993.

BACKGROUND OF THE INVENTION

1. Field of the Invention

The present invention relates to apparatus for the live scanning of fingerprint images and more particularly to a portable apparatus for the scanning and capture of fingerprint images and the wireless transmission of said images to a central location for identity verification.

2. Description of Background Material

Over the years, the most commonly used techniques for both identity verification and the identification of potential crime suspects have been the use of fingerprints and photographs or "mug shots".

Originally, fingerprinting was done by inking a suspect's finger and applying the inked finger to paper. As can be readily understood, fingerprint information in this form was difficult to use. Making a fingerprint match was an extremely time-consuming task. Digital technology significantly advanced the art of fingerprinting. Inked images could be scanned and the image digitized and recorded in a manner that could later be searched in a reasonably expeditious manner by computer. Problems arose, however, due to the quality of inked images. Over- and under-inking resulted in blurred or vague images, thus rendering the digitized information useless. Further, the process of scanning an inked image was relatively time consuming.

These and other problems led to "live scanning". According to live scanning techniques, the fingerprint of a suspect is scanned directly from the suspect's finger, as opposed to being scanned from an inked image of the print. More specifically, live scans are those procedures which capture fingerprint ridge detail in a manner which allows for the immediate processing of the fingerprint image with a computer. Original work in the field dates back to original patents filed in 1964 concerning techniques used to capture high contrast images of fingerprint for photographic or digital capture of fingerprints.

Since their introduction, live scans have become an important tool for law-enforcement. The live scan has the potential to overcome inherent weaknesses in the ink capture of fingerprints and provide immediate transmission of fingerprint images; and allow for image enhancement if necessary.

These characteristics provide law-enforcement with the ability to improve the quality of the fingerprint data base, thereby improving the likelihood that identifications can be made either from latent fingerprints or from identity verification checks. In addition, live scan fingerprints are easily adaptable to computerized storage and processing techniques, increasing cooperation and fingerprint data transfer between various police agencies.

Systems which optically or optically and mechanically generate fingerprint images are in use. Several such fingerprinting systems are disclosed in Fishbine et al. (U.S. Pat. Nos. 4,811,414 and 4,933,976); Ruell (German Patent No. 3423886 A1); Becker (U.S. Pat. No. 3,482,498); McMahon (U.S. Pat. No. 3,975,711); Schiller (U.S. Pat. Nos. 4,544,267 and 4,322,163); Marcus (U.S. Pat. No. 4,533,837) and White (U.S. Pat. No. 3,200,704).

While the fingerprinting systems disclosed in the foregoing patents are capable of providing optical or optical and mechanical fingerprint images, said systems are only suitable or use at a central location such as the police station. It is evident that there is also a need for a portable and lightweight fingerprint scanning system which can optically generate fingerprint images in the field. Such a portable system would be ideal for traffic officers and other law enforcement professionals who want to perform an immediate identity and background check on an individual while in the field. It is also evident that there is a need for a portable fingerprint system which has the capability for the wireless transmission of fingerprint images captured in the field to a central facility for identity verification using an automated fingerprint identification system.

It is further evident that there is a need for a portable fingerprint system which also includes the capability of capturing a photographic image or "mug shot" for wireless transmission to a central facility for identity verification using systems such as the FBI National Crime Information Center Network.

SUMMARY OF THE INVENTION

The present invention is a portable and lightweight fingerprint scanning apparatus which can optically scan and record fingerprint images in the field and transmit said images to a mobile unit for processing and subsequent wireless transmission to a central location for the purpose of providing immediate identity and background checks on the individual being fingerprinted. The apparatus of the present invention includes a fingerprint scanner for capturing a fingerprint image, a camera for capturing a photographic image of a person or a scene and transmitting means for transmitting the fingerprint image and the photographic image to a mobile unit. In the preferred embodiment the present invention includes a highly integrated camera with a superior signal to noise ratio and an infrared lighting source for illuminating a person or scene in low ambient light situations. An especially preferred embodiment of the present invention also provides the ability to preview the fingerprint and "mug shot" images on a display screen and to control transmission and processing of the fingerprint and "mug shot" images by the mobile unit using a terminal or keypad located on the portable fingerprint scanning apparatus. The present invention allows law enforcement professionals to perform immediate identity and background checks on an individual while in the field.

DETAILED DESCRIPTION OF THE PREFERRED EMBODIMENTS

In the following Detailed Description of the Preferred Embodiments, reference is made to the accompanying Drawings which form a part hereof, and in which is shown by way of illustration specific embodiments in which the invention may be practiced. It is to be understood that the other embodiments may be utilized and structural changes may be made without departing from the scope of the present invention.

Figure 1:
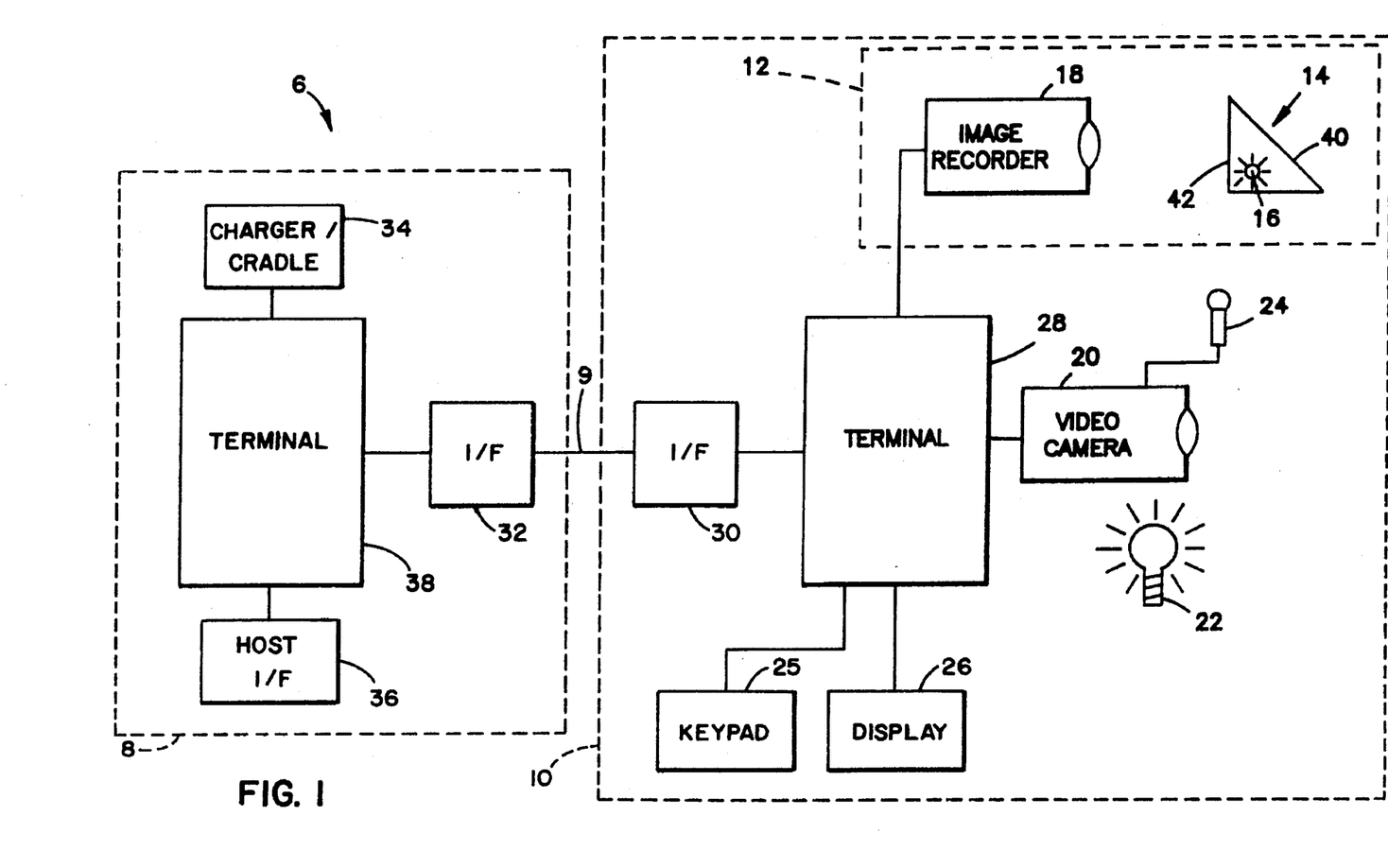
FIG. 1 is a block diagram representation of an apparatus which can be used to capture fingerprint and photographic images in the field and transmit said images to a central location for identification verification in accordance with the present invention.

A portable identification verification system 6 which can be used to optically capture and produce fingerprint and other photographic images in accordance with the present invention is illustrated generally in FIG. 1. System 6 includes a base unit 8 connected over a data transmission interface 9 to a portable image collection unit 10.

Base unit 8 includes an interface circuit 32, a charger/cradle 34 and a host interface 36 all interfaced to terminal 38. Portable image collection unit 10 includes fingerprint scanner 12, camera 20, keypad 25, display 26 or interface circuit 30 all interfaced to terminal 28. In one preferred embodiment, terminals 28 and 38 are based on the Motorola 68340 microprocessor in order to reduce the number of peripheral circuits required. In addition, in one preferred embodiment, terminals 28 and 38 include one or more SCSI interfaces, one or more frame grabbers, a high speed serial link and a system interface.

Fingerprint scanner 12 consists of a finger prism 14 and a scanning camera 18. Fingerprint images from the portion of a finger placed in contact with receiving surface 40 of finger prism 14 are imaged by scanning camera 18. Scanning camera 18 includes a lens and imaging medium (not separately shown). Fingerprint images generated by fingerprint scanner 12 can be displayed on display 26 and transmitted by interface circuit 30 to base unit 8 for further processing. In the preferred embodiment, base unit 8 is mounted in a mobile unit such as a patrol car. Camera 20 generates a photographic image, or "mug shot", of the person being fingerprinted. Camera 20 can also be used to capture a picture of the scene being investigated. The image generated by camera 20 can be displayed on display 26 or transmitted by interface circuit 30 to base unit 8 for viewing or recording.

Keypad 25 can be used by an operator to interface with portable identification verification system 6. Through keypad 25, an operator can control the various functions supported by transmitter 28. For instance, keypad 25 can be used to display an image from fingerprint scanner 12 or camera 20 on display 26. Keypad 25 can also be used to transmit control signals to base unit 8 over data transmission interface 9 or to transmit images from terminal 28 to terminal 38 over interface 9. In one embodiment, keypad 25 is a four button, back-lit keypad having the following functions:

MODE: Toggles between fingerprint and mug sot mode (the system powers up in mug shot mode).
CAPTURE: Causes image collection unit 10 to freeze the current image (fingerprint or mug shot) and send it to base unit 8 for processing.
MENU: Causes the system to enter "menu" mode, blanks display 26 and lists a number of functions with the topmost function high-lighted. Subsequent depressions of the MENU button scrolls the list to high-light alternate functions.
SELECT: Causes the high-lighted function in the display menu to be performed.

In an alternate embodiment, a twelve key pad similar in layout to the dual-tone multifrequency (DTMF) keys of a touch tone telephone can be used in addition to the four button keypad to provide greater flexibility in data entry. Even further flexibility in input/output can be gained by substituting a pen-based interface for keypad 25 or by installing a small scale QWERTY keyboard (as in a notebook computer). Other input/output devices can be used to supplement or replace keyboard 25. For instance, keypad 25 could be replaced with a magnetic card reader or a bar code scanner. In addition, a breathalizer circuit might prove particularly advantageous for processing people suspected of driving while intoxicated. In the preferred embodiment, each such input/output device is treated as a peripheral device by a processor in terminal 28.

In the preferred embodiment, portable image collection unit 10 sits in charger/cradle 34 when not in use. When unit 10 is removed from charger/cradle 34, it powers up and can be used to acquire images. In that embodiment, unit 10 is encased in a single housing and is designed to be small enough and light enough for use in the field by such people as law enforcement personnel.

In one preferred embodiment, image collection unit 10 may be implemented as a two-part system; the top half holds the optics, computer systems and operator controls and the bottom half is designed as a removable center channel having various options for interconnection to base unit 8 (tether, RF link, disk drive, etc.). Both halves of unit 10 connect together via, for instance, a PCMCIA interface for standardization.

In one embodiment, the two-part system is implemented as a two-part injection-molded case with the top half of the case having a writing surface and keypad 25 and the bottom half being essentially a shell. One example of such a housing is shown, for example, in FIG. 5. In the unit 10 of FIG. 5, housing 52 has two side surfaces 53, a top surface 54, a bottom surface 55, a front end surface 56 and a back end surface 57.

Figure 5:
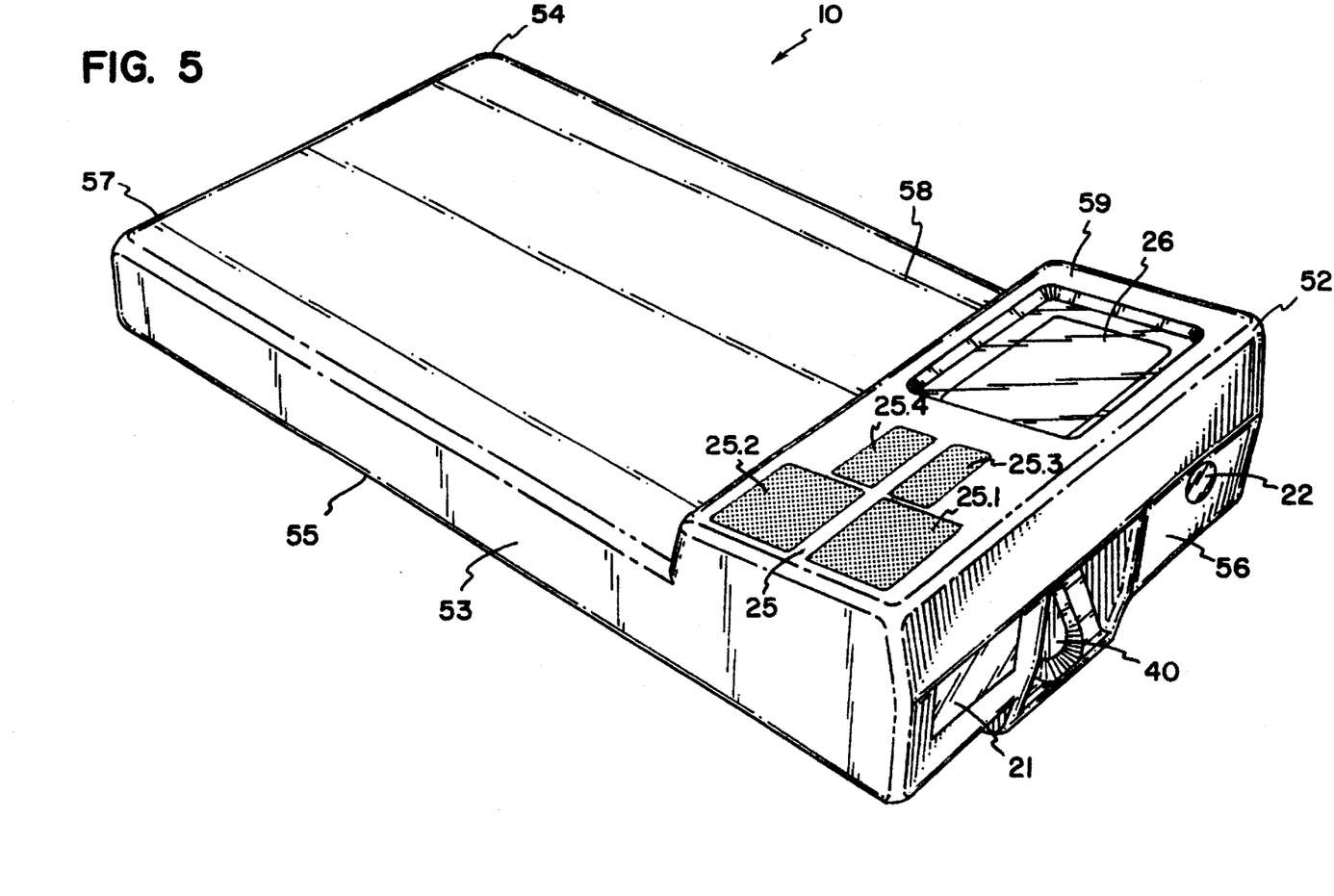
FIG. 5 is a representation of one embodiment of a package used to house the portable image collection unit of FIG. 1.

Top surface 54 includes a writing surface 58 and a user interface surface 59. User interface surface 59 contains display 26 and keypad 25. Keypad 25 has four buttons 25.1–4 corresponding to the MODE, CAPTURE, MENU and SELECT buttons, respectively, described above. In one preferred embodiment, writing surface 58 includes a clip (not shown) for clipping a tablet of citations to writing surface 58.

Front end surface 56 includes illumination source 22, a filter 21 for camera 20 and finger receiving surface 40 of fingerprint scanner 12. In an alternate embodiment, camera 20 and illumination source 22 may be placed adjacent to each other so as to share filter 21.

In the preferred embodiment, housing 52 can be screwed together to allow for repair if needed. The interface circuit 30 option selected should screw into the center channel (not shown) of the bottom case. In the preferred embodiment, the screws should extend all the way into the top half of the case for mechanical strength. In a further preferred embodiment, a PCMCIA or SCSI connector is provided on the back end surface 57 in order to permit connection to an external device.

In operation, image collection unit 10 is carried, for example, by a police officer to the scene of an investigation. Persons to be identified are photographed and fingerprinted, the scene is photographed and unit 10 transfers the resulting images to base unit 8 in the patrol car. From there the mug shot, scene and fingerprint information can be compressed and sent to the police station for comparison against existing mug shot and fingerprint images or for review by other investigators. By expediting the process of obtaining and verifying fingerprint and mug shot images, system 6 provides a better and faster method of verifying an individual's identity. This expedited identification not only fosters efficiency in the investigation but also provides knowledge critical to protecting an officer's safety.

Figure 2:
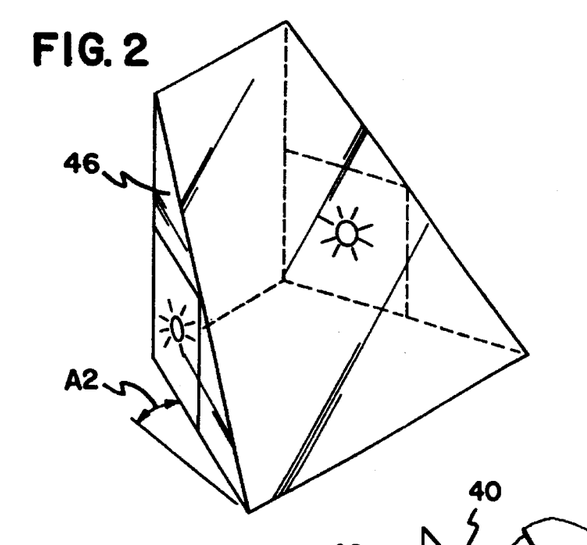
FIG. 2 is a perspective view of the finger prism shown in FIG. 1.
Figure 3:
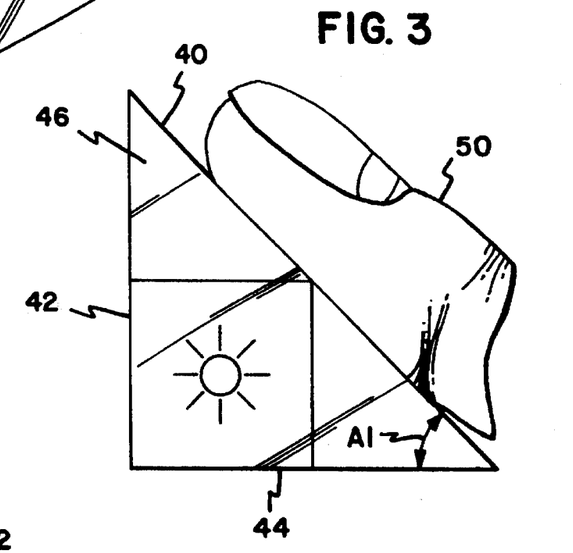
FIG. 3 is a side view of the finger prism shown in FIG. 2.
Figure 4:
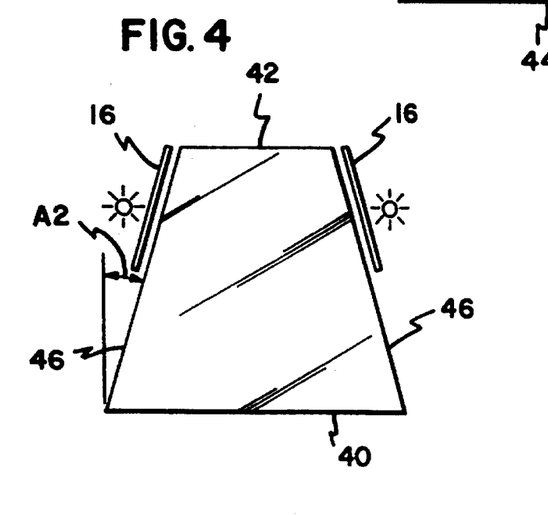
FIG. 4 is a top view of the finger prism shown in FIG. 2.

Optical devices such as finger prism 14 are well known and disclosed, for example, in McMahon U.S. Pat. No. 3,975,711; White U.S. Pat. No. 3,200,701; and Fishbine et al., U.S. Pat. Nos. 4,792,226, 4,811,414 and 4,933,976. These devices use the optical principle of total internal reflection. When a finger is positioned on finger receiving surface 40 (a planar surface in the preferred embodiment but a curved surface could be used), an optical image of the ridge and valley pattern on the surface of the finger (i.e., the fingerprint) is propagated from image propagation surface 42. Finger prism 14 is best described with reference to FIGS. 2–4. Finger prism 14 is an optical device fabricated of a light propagating material, such as plastic, glass or a combination thereof, which is characterized by an index of refraction. As shown, finger prism 14 has a sloping upper surface or finger receiving surface 40 and a rear or image propagating surface 42. Finger prism 14 also includes a bottom surface 44 and two side surfaces 46. Illumination is provided on side surfaces 46 by illumination source 16. In the preferred embodiment, illumination source 16 consists of light-emitting diodes attached to side surfaces 46 of finger prism 14. Bottom surface 44 is coated with an opaque material such as black paint. Finger prism 14 has overall dimensions such that finger receiving surface 40 can receive and image at least one finger 50. Image propagating surface 42 is perpendicular to bottom surface 44. In one preferred embodiment in which finger prism 14 is manufactured of acrylic material, A1 is 45° and A2 is 20°. Finger prism 14 is designed to utilize the optical principle of frustration of total internal reflection. These optical principles are described in Fishbine et al. U.S. Pat. No. 4,811,414 which is hereby incorporated by reference. These properties result in a visual fingerprint image of a finger placed on image receiving surface 40 being propagated through image propagation surface 42. The fingerprint image has "light" areas corresponding to ridges of the fingerprint and "dark" areas corresponding to valleys of the fingerprint. Other means or optical devices which provide fingerprint images can also be used.

Scanning camera 18 is mounted with respect to finger prism 14 and configured in such a manner that its field of view encompasses the entire image propagation surface 42. Scanning camera 18 continuously images fingerprint images through its objective lens onto its image recording media resulting in an image representative of the light reflected from the parts of the finger 50 in contact with the image receiving surface 40. The recorded image looks like the photographic negative of the fingerprint image. In one embodiment, scanning camera 18 is a video camera that continually images fingerprint images through its objective lens, and generates frames of video signals representative thereof. Any commercially available video camera, such as a Model XC-77 video camera manufactured by Sony Corporation, can be used. In such an embodiment, a frame grabber (not shown) in terminal 28 receives the standard video signal from the video camera, converts the video signal to a series of digitized frames and stores the digitized frames to terminal 28 memory for display and/or transmission to base unit 8.

The embodiment of scanning camera 18 described above has some shortcomings. Typically, available video cameras are constrained to video signal outputs which fit into one of the popular television signal formats. For instance, a typical video camera produces a NTSC video signal. Therefore, video resolution is limited to the resolution available to an NTSC video camera. This level of video resolution has been adequate but, due to the requirement of fitting the NTSC format, there were no apparent options for increasing video resolution. In addition, the approach of using a commercial video camera introduces two sources of image degradation. First, since most commercial video cameras are based on a CCD element, the camera must first convert each pixel in the CCD array into the NTSC scan line format. The resulting scan line is then sent over a RS170 line to the frame grabber in terminal 28. This conversion from the CCD pixel format to the NTSC scan line format and the subsequent transmission of that video signal to frame grabber results in a loss of about 20% of the information. This approach also places a limit on the pixel scanning rate due to the need to conform to the NTSC standards.

Figure 6:
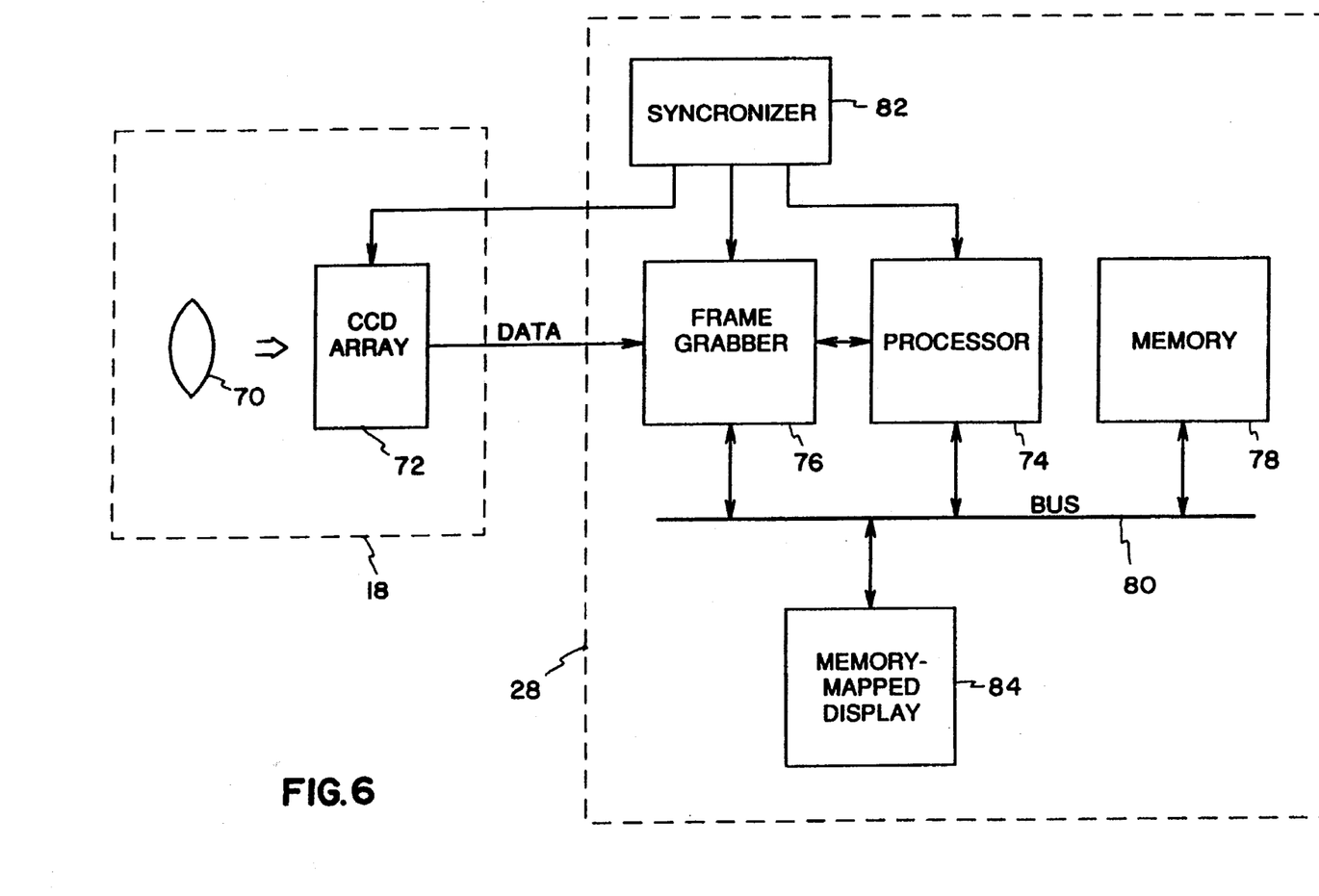
FIG. 6 is an electrical block diagram representation of an integrated fingerprint scanning camera which can be used advantageously in the system shown in FIG. 1.

An alternate embodiment of scanning camera 18 which overcomes these limitations to produce fingerprint images having a superior signal to noise ratio is shown generally in the electrical block diagram of FIG. 6. In the system of FIG. 6, scanning camera 18 is formed by placing a lens 70 so that light from image propagating surface 42 is focussed on CCD array 72. In contrast to the video camera implementation described above, in the system of FIG. 6 an output of CCD array 72 is connected directly to terminal 28. In one embodiment, terminal 28 is formed by interconnecting a processor 74 with digitizer 76, memory 78, synchronization circuit 82 and memory mapped display card 84. Processor 74 communicates with digitizer 76, memory 78 and memory mapped display card 84 over a bus 80. Operation of processor 74, digitizer 76 and CCD array 72 is synchronized by clock signals generated by synchronization circuit 82.

In one embodiment, CCD array 72 is an array of pixel elements 73.1 through 73.p distributed as an m×n array of pixel elements (where p=m×n). In one such embodiment, a 768×494 pixel CCD array 72 provides high resolution over a field of view encompassing image propagating surface 42. CCD array 72 is connected directly to digitizer 76 so that a discrete analog level associated with a voltage level present at each pixel 73 in CCD array 72 is transferred directly to digitizer 76. A clock signal generated by synchronization circuit 82 clocks CCD array 72 in order to serially shift to digitizer 76 in terminal 18 the discrete analog signal associated with each of the pixel elements 73. Digitizer 76, under the control of processor 74, digitizes the analog voltage sent by CCD array 72 and stores it to memory 78. Processor 74 can then access memory 78 in order to display or transmit the resulting fingerprint image.

In one such embodiment, CCD array 72 is clocked continuously by synchronization circuit 82 in order to produce a continuous stream of analog voltage levels to digitizer 76. Digitizer 76 digitizes the analog stream in order to determine the voltage level corresponding to each pixel element 73 in CCD array 72 and presents the resulting image to memory 78 over bus 80. Processor 74 in turn accesses memory 78 in order to obtain each image and converts the series of images into a fingerprint image. The resulting fingerprint image can then be directed to interface 30 for transmission to base unit 8 or through memory mapped display circuit 84 to display 26 for viewing by the operator.

One method of producing a fingerprint image from a series of digitized images is described in Fishbine et al., U.S. Pat. No. 4,933,976, which patent is hereby incorporated by reference. Fishbine et al. discloses a method of building a composite fingerprint image from a plurality of arrays of slice data characteristic of adjacent and overlapping two-dimensional slices of the fingerprint image. That method can be used advantageously with either of the two scanning camera implementations described above.

The tight integration of CCD array 72 and digitizer 76 as shown in FIG. 6 results in a 25% increase in signal-to-noise in the digitized image. In addition, since CCD array 72 and digitizer 76 are controlled by the same synchronization circuit 82, the resulting one-to-one match in pixels results in a 33% gain in resolution. Finally, since synchronization circuit 82 is not limited to a standard format, CCD array 72 can be scanned at its maximum rate. As a result, the system shown in FIG. 6 can achieve a much higher pixel rate than that possible when one is constrained to a standard video format.

In an alternate embodiment, where a high resolution image is not required, a slower, less expensive CCD array 72 could be used. Such an approach would also reduce cost in digitizer 76 and in the remaining digital components. Alternatively, scanning camera 18 can be formed by other types of electronic cameras or imagers (such as an electrophotographic recording device).

The digitized output of scanning camera 18 can be viewed on display 26. In the preferred embodiment, display 26 is a Hitachi LCD display having 240×240 pixels, eight level grey scale and an approximate 2×2.7 inch viewing area. The digitized output of scanning camera 18 can also be transferred to base unit 8 over a tether cable having a power cord and one or more data lines or can be wirelessly transmitted by a spread spectrum embodiment of interface circuit 30. A preferred tether cable is a four conductor cable in which two conductors are shielded and the other two unshielded. The two shielded conductors form a high speed differential pair for data transfer. On unshielded conductor is used to supply power; the other is used to indicate the direction of data transmission.

In the preferred embodiment, the end of the tether cable that attaches to image collection unit 10 does not need a connector. It is permanently attached through the center channel of housing 52 to interface 30. The other end of the cable should, however, have a connector; an Amphenol 5-pin screw-lock connector has been found to have good rough-handling characteristics. In the preferred embodiment the center channel adapter includes a 7.2 V regulator.

When a tether is not used, battery power must be provided to image collection unit 10. In the preferred embodiment, a rechargeable battery pack is connected to unit 10 through the center channel adapter. Such a battery pack must be provided for all non-tether embodiments. It has been found to be particularly advantageous to include the battery pack as part of the adapter module for all non-tether data transfer embodiments.

When the operator desires to "capture" a fingerprint image being previewed on display 26, the operator will actuate a key on keypad 25 (such as the CAPTURE key described above). In response, terminal 28 generates a signal transmitted by interface circuit 30 to base unit 8 indicating that capture and processing of the fingerprint image should be initiated. Upon receiving the signal from terminal 28, base unit 8 processes the fingerprint image in accordance with methods described in U.S. Pat. Nos. 4,811,414 and 4,933,976, which are hereby incorporated by reference. After image processing and compression in base unit 8, the image can be transmitted wirelessly to a unit at a central facility, such as a police station, for identity verification using an automated fingerprint identification system such as the FBI's National Crime Information Center Network.

In an alternate embodiment, nonvolatile memory such as a fixed disk drive or a flash memory card can be attached to interface 30 in lieu of the tether or the wireless transceiver. Images captured by image collection unit 10 are stored to the nonvolatile memory for later transmission to base unit 8. In one such embodiment, power for image collection unit 10 is provided by a battery supplied as part of the nonvolatile memory package. Such an embodiment has the advantage of almost unlimited range from base unit 8.

In one embodiment, camera 20 is a standard video camera that continuously receives images through its objective lens, and generates frames of video signals representative thereof. Commercially available video cameras using conventional rasters and scanning rates can be used. Camera 20 may, for instance, be implemented with a standard video camera such as Model XC-77 manufactured by Sony Corporation. Any commercially available video camera capable of obtaining a full face or "mug shot" image would be suitable.

Figure 7:
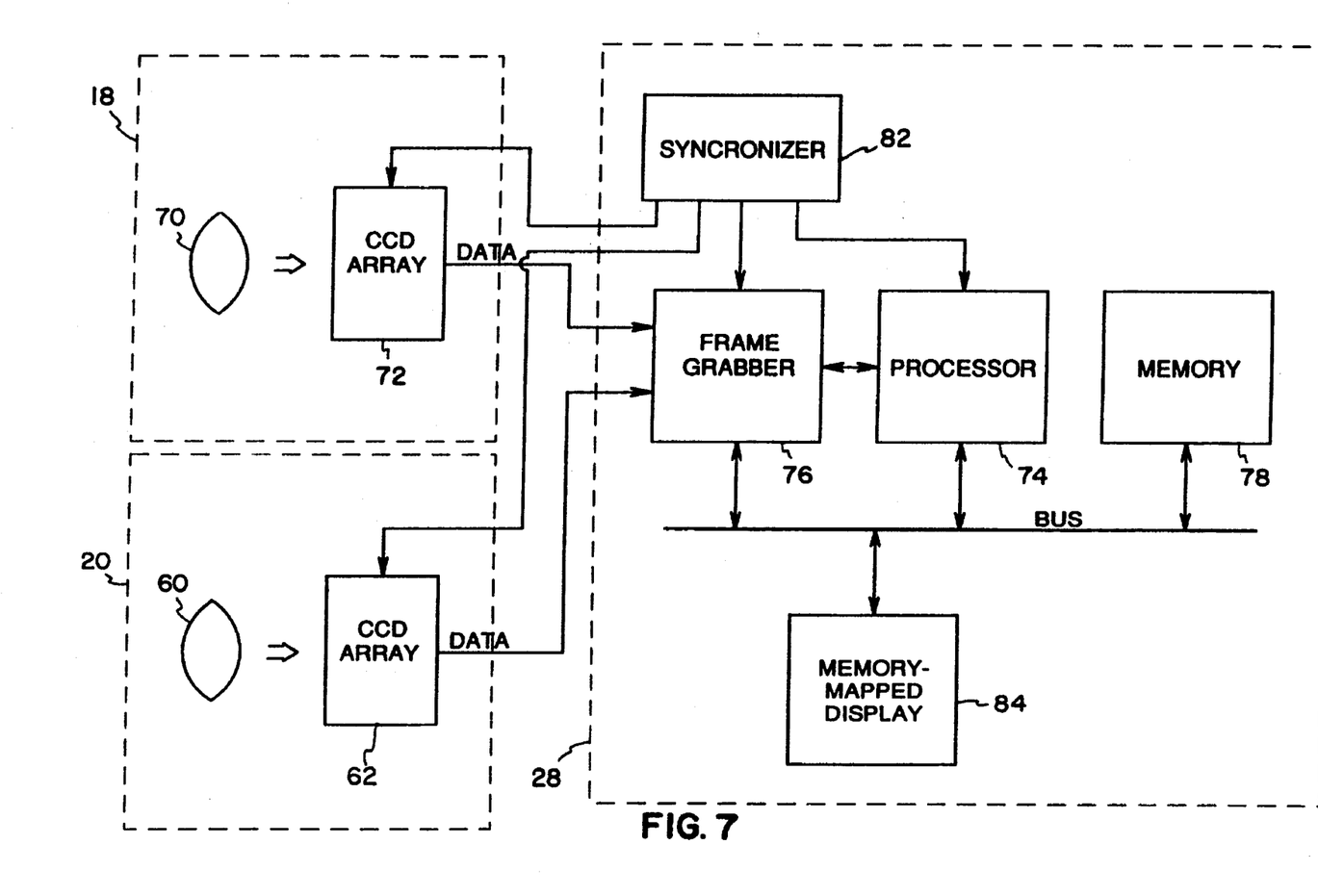
FIG. 7 is an electrical block diagram representation of an integrated pair of cameras which can be used advantageously to capture both fingerprint and mug shot images in the system shown in FIG. 1.

In an alternate embodiment, such as that shown generally in FIG. 7, camera 20 may be implemented with a lens 60 and a CCD array 62 in a manner similar to that described for scanning camera 18 in FIG. 6. In the embodiment shown in FIG. 7, both camera 20 and scanning camera 18 are implemented with CCD arrays connected directly to frame grabber board 76. As in FIG. 6, data transferred from CCD arrays 62 and 72 to frame grabber 76 is in the form of pixel analog voltages rather than the traditional video signal. Some additional cost savings can be had by multiplexing the data line from CCD array 62 and CCD array 72 so that frame grabber board 76 processes only one image at a time.

In addition to lens 60 and CCD array 62, camera 20 of FIG. 7 would also require some sort of focusing mechanism (not shown). Well known manual focusing mechanisms could be used. In addition, an autofocusing (AF) lens could be used as lens 60 to automate the focussing of camera 20.

In one embodiment of an autofocus system for camera 20, passive sensing is used to focus an autofocus version of lens 60. In passive sensing the image itself is used (rather than an ultrasonic or infrared system) to determine if camera 20 is focussed. According to the method, horizontal scans of image data are used to determine whether an image is in focus. Each horizontal scan line is examined and the autofocus mechanism of lens 60 is adjusted to maximize the number of edges. In one embodiment, the serial stream of data from CCD array 62 to frame grabber 76 is masked to obtain the area of focus interest. The resulting image is run through two second-order differentiators (Butterworth highpass) to obtain an edge-detect signal in the horizontal dimension, then fed to a slow-decay peak detector. The voltage peak at this point is highest when the video image is sharpest; i.e., in focus. This signal is fed into a slow differentiator and comparator, which generates an error signal of the proper polarity to drive an autofocus DC motor attached to lens 60. In such an approach a problem does, however, exist when the peak differentiator output falls below the comparator threshold voltage; there may need to be some initial "boot" movement to the AF system. In an alternate embodiment, this entire algorithm could be reproduced in software to reduce parts count.

The two second-order differentiators are used to allow a light sensing output for use in determining auto-light sensing. The first second-order output is related to the contrast of the video image, and can be peak detected similarly to the above to obtain "light needed" output.

As in the case of images produced by scanning camera 18, images generated by camera 20 may be previewed on display 26 and transferred over a tether cable or by wirelessly transmission to base unit 8. When the operator viewing the image in display 26 desires to capture a "mug shot" image, the operator will actuate a key on keypad 25. In response, terminal 28 sends the digitized image via interface circuit 30 to base unit 8 for storage.

In an alternate embodiment, terminal 18 may be implemented so that interface circuit 30 sends a video signal to base unit 8. In such a system, camera 20 could be used to videotape a crime scene or to capture video of a person suspected of driving while under the influence of alcohol or drugs. The video signal transmitted by interface circuit 30 to base unit 8 could also be recorded on a video tape recorder (not shown) attached to base unit 8. In another embodiment, it may be advantageous to digitize frames of the video signal and save the resulting digitized frames to a fixed disk or other nonvolatile mass storage device.

A video logging recorder could also be used with the digital implementation of portable identification verification system 6. In one such embodiment, a video recorder connected to terminal 38 of base unit 8 is used to store digital images transferred from image collection unit 10. When unit 10 is lifted from the cradle, the logging recorder is initialized and is put into pause mode. When a captured image is received by base unit 8, the recorder could be taken out of pause for one second to record the still frame equivalent of the image. In such an embodiment, a two hour tape could be used to store up to 7200 images. In an alternate embodiment, an image stored on the logging recorder can be transferred from base unit 8 to unit 10. For instance, mug shot images stored on the logging recorder could be reviewed on display 26 by an officer interviewing a suspect or by witnesses while their memories are still fresh.

Camera 20 may also be connected to microphone 24 and be provided with an illumination source 22. In one embodiment, cameras 18 and 20 are formed with CCD arrays 70 and 60 which operate down into the infrared region. In such an embodiment, illumination source 22 is formed from a plurality of infrared light emitting diodes in order to provide unobtrusive illumination capable of capturing images of subjects or scenes up to 30 feet away in total darkness.

In the preferred wireless transmission embodiment, interface circuit 30 of image collection unit 10 and the corresponding receiver in base unit 8 use spread spectrum radio frequency transmission. But any other wireless transmission means such as microwave or infrared transmission could be utilized.

Although the present invention has been described with reference to the preferred embodiments, those skilled in the art will recognize that changes may be made in the form and detail without departing from the spirit and scope of the invention.

What is claimed:

1. A portable apparatus for identification verification, comprising:
    a portable image collection unit including:
        a fingerprint scanner comprising a finger prism having an opaque bottom surface, a finger receiving surface and two side surfaces; a light for illumination of the finger prism so that a fingerprint image can be propagated therefrom; a camera mounted within the portable apparatus so as to be capable of receiving fingerprint images propagated from the finger prism and a recording component for capturing the received fingerprint images;
        image capturing means for obtaining an image of the person being fingerprinted;
        display means for viewing an image from a group of images including the fingerprinted person's image and the captured fingerprint image; and
        terminal means, connected to the fingerprint scanner, image capturing and display means, for selecting the image to be viewed;
    a base unit connected to the terminal means, for receiving the selected image, and operative in digitizing the selected image wherein the portable image collection unit is selectively removable from the base unit.

2. The apparatus according to claim 1, wherein the terminal means comprise transmission means for transmission of the fingerprinted person's image and the captured fingerprint images to the base unit means.

3. The apparatus according to claim 2, wherein the transmission means comprise means for wireless transmission of the fingerprinted person's image and the captured fingerprint images.

4. The apparatus according to claim 2, wherein the transmission means comprise a tether cable having separate power and data lines.

* * * * *